United States Patent [19]

Glenn

[11] 4,248,090
[45] Feb. 3, 1981

[54] APPARATUS FOR ULTRASONICALLY IMAGING A BODY

[75] Inventor: William E. Glenn, Ft. Lauderdale, Fla.

[73] Assignee: New York Institute of Technology, Old Westbury, N.Y.

[21] Appl. No.: 890,377

[22] Filed: Mar. 27, 1978

[51] Int. Cl.³ .............................................. G01N 29/04
[52] U.S. Cl. ...................................... 73/620; 128/660
[58] Field of Search .......... 128/2 V, 2.05 Z, 660–663; 73/642, 618–626; 340/1 R, 8 FT, 8 R; 367/141, 150–151, 153–155

[56] References Cited

U.S. PATENT DOCUMENTS

| | | | |
|---|---|---|---|
| 3,159,023 | 12/1964 | Steinbrecher | 128/2 V X |
| 3,251,219 | 5/1966 | Hertz et al. | 128/2 V X |
| 3,847,016 | 11/1974 | Ziedonis | 128/660 |
| 3,888,238 | 6/1975 | Meindl et al. | 128/663 |
| 3,889,227 | 6/1975 | Takamizawa et al. | 343/100 LE |
| 3,918,024 | 11/1975 | Macovski | 128/660 |
| 3,936,791 | 2/1976 | Kossoff | 340/1 R |
| 4,001,766 | 1/1977 | Hurwitz | 73/644 |
| 4,034,744 | 7/1977 | Goldberg | 128/2 V |
| 4,070,905 | 1/1978 | ,ossoff | 128/660 |
| 4,084,582 | 4/1978 | Nigam | 73/620 X |
| 4,094,306 | 6/1978 | Kossoff | 128/660 |
| 4,103,677 | 8/1978 | Lansiart et al. | 128/2 V |
| 4,110,723 | 8/1978 | Hetz et al. | 73/620 X |
| 4,137,777 | 2/1979 | Haverl et al. | 73/626 X |

OTHER PUBLICATIONS

Wells, P.N.T., "Biomedical Ultrasonics", Academic Press, New York, 1977, p. 39.
Mountford, R. A. et al, "Semi-Automatic Transducer Movement for Ultrasonic Compound B Scanning", MBE, vol. 12, No. 6, Mar. 1974, pp. 227–232.

*Primary Examiner*—William E. Kamm
*Assistant Examiner*—Francis J. Jaworski
*Attorney, Agent, or Firm*—Martin Novack

[57] ABSTRACT

The disclosure is directed to an apparatus for ultrasonically investigating a section or slice of a body by transmitting ultrasonic energy into the body and determining the characteristics of the ultrasonic energy reflected therefrom. A transducer is coupled to an energizing means and generates a beam of ultrasonic energy. The beam is focused and scanned across the body being investigated along the plane of the slice of the body to be imaged. A feature of the present invention is that the ultrasound-generating transducer has a generally elliptical shape elongated along the direction of the scan. The result is a scanned focused spot which is elongated in a direction normal to the direction of scan. The thickness of the investigated "slice" is therefore substantially larger (preferably at least twice as large) as a resolution element in the direction of scan.

101 Claims, 8 Drawing Figures

APPARATUS FOR ULTRASONICALLY IMAGING A BODY

BACKGROUND OF THE INVENTION

This invention relates to ultrasonic systems and, more particularly, to apparatus for imaging sections of a body by transmitting ultrasonic energy into the body and determining the characteristics of the ultrasonic energy reflected therefrom. The subject matter of this application is related to subject matter disclosed in my copending U.S. patent application Ser. No. 890,378 entitled "Ultrasonic Imaging Apparatus", filed of even date herewith and assigned to the same assignee as the present application.

In recent years ultrasonic techniques have become more prevalent in clinical diagnosis. Such techniques have been utilized for some time in the field of obstetrics, neurology and cardiology, and are becoming increasingly important in the visualization of a number of different body portions, for example the scanning of breasts to detect tumors.

Various fundamental factors have given rise to the increased use of ultrasonic techniques. Ultrasound differs from other forms of radiation in its interaction with living systems in that it has the nature of a mechanical wave. Accordingly, information is available from its use which is of a different nature than that obtained by other methods and it is found to be complementary to other diagnostic methods, such as those employing X-rays. Also, the risk of tissue damage using ultrasound appears to be much less than the apparent risk associated with ionizing radiations such as X-rays.

The majority of diagnostic techniques using ultrasound are based on the pulse-echo method wherein pulses of ultrasonic energy are periodically generated by a suitable piezoelectric transducer such as a lead zirconate-titanate ceramic. Each short pulse of ultrasonic energy is focused to a narrow beam which is transmitted into the patient's body wherein it eventually encounters interfaces between various different structures of the body. When there is a characteristic impedance mismatch at an interface, a portion of the ultrasonic energy is reflected at the boundary back toward the transducer. After generation of the pulse, the transducer operates in a "listening" mode wherein it converts received reflected energy or "echoes" from the body back into electrical signals. The time of arrival of these echoes depends on the ranges of the interfaces encountered and the propagation velocity of the ultrasound. Also, the amplitude of the echo is indicative of the reflection properties of the interface and, accordingly, of the nature of the characteristic structures forming the interface.

There are various ways in which the information in the received echoes can be usefully presented. In one common technique, the electrical signal representative of detected echoes are amplified and applied to the vertical deflection plates of a cathode ray display. The output of a time-base generator is applied to the horizontal deflection plates. Continuous repetition of the pulse/echo process in synchronism with the time-base signals produces a continuous display, called an "A-scan", in which time is proportional to range, and deflections in the vertical direction represent the presence of interfaces. The height of these vertical deflections is representative of echo strength.

Another common form of display is the so-called "B-scan" wherein the echo information is of a form more similar to conventional television display; i.e., the received echo signals are utilized to modulate the brightness of the display at each point scanned. This type of display is found especially useful when the ultrasonic energy is scanned transverse the body so that individual "ranging" information yields individual scan lines on the display, and successive transverse positions are utilized to obtain successive scan lines on the display. The two-dimensional B-scan technique yields a cross-sectional picture in the plane of the scan, and the resultant display can be viewed directly or recorded photographically or on magnetic tape.

While successes have been achieved in the field of ultrasonic imaging, there are a number of problems which need to be overcome in obtaining high quality ultrasonic images in a convenient, reliable and cost-effective manner. Regarding problems which have been partially overcome, it is known, for example, that ultrasound is almost totally reflected at interfaces with gas. This has led to the use of coupling through a fluid such as water or the use of a direct-contact type of transducer. The latter technique may give rise to problems when attempting to image structures such as arteries which may be only a few millimeters below the skin surface, the contact imaging causing aberrations in the near field of the transducer. Coupling through a fluid offers advantage over direct-contact in this respect, but leads to various design problems and cumbersome generally non-portable structures which are inconvenient to use, especially when attempting to register them accurately on a patient. Some techniques involve immersing the patient in water or obtaining appropriate contact of the body part with a bulky water tank wall.

The need to scan the ultrasonic beam in two dimensions gives rise to problems of bulkiness and difficulty of handling in the scanning unit. In the co-pending U.S. patent application Ser. No. 665,898, assigned to the same assignee as the present invention, there is disclosed a type of apparatus which provides improved convenience as compared to most water coupled imaging techniques. The apparatus disclosed therein has a console which typically includes a timing signal generator, energizing and receiving circuitry, and a display/-recorder for displaying and/or recording image-representative electronic signals. A portable scanning module, suitable for being hand held, has a fluid-tight enclosure having a scanning window formed of a flexible material. A transducer in the portable scanning module converts energy from the energizing circuitry to ultrasonic energy and also converts received ultrasound echoes back into electrical signals which are coupled to the receiver circuitry. A focusing lens is coupled to the transducer, and a fluid, such as water, fills the portable scanning module in the region between the focusing lens and the scanning window. A reflective scanner is disposed in the fluid, and the driving motor, energized in synchronism with the timing signals, drives the reflective scanner in periodic fashion.

A scanning module of the type disclosed in the referenced co-pending application is advantageous in that it is portable and relatively light and easy to handle as compared to other prior art scanners known to applicant. However, it would be most advantageous to develop a portable ultrasonic scanning module which is smaller, lighter, easier to handle and use, requires less mechanical drive power, and is otherwise operationally advantageous as compared to prior art scanners.

It is an object of the present invention to improve upon existing ultrasonic scanners, and especially ultrasonic scanners of the portable hand-held type.

SUMMARY OF THE INVENTION

The present invention is directed to an apparatus for ultrasonically investigating a section or slice of a body by transmitting ultrasonic energy into the body and determining the characteristics of the ultrasonic energy reflected therefrom. In accordance with the invention, means are provided for generating an energizing signal. A transducer is coupled to the energizing means and generates a beam of ultrasonic energy. Axially symmetrical focusing means are provided for focusing the beam, and means are provided for scanning the beam across the body being investigated along the plane of the slice of the body to be imaged. A feature of the present invention is that the ultrasound-generating transducer is elongated along the direction of the scan and has, for example, a generally elliptical shape. The result is a scanned focused spot which is elongated in a direction normal to the direction of scan. The thickness of the investigated "slice" is therefore substantially larger (preferably at least twice as large) than a resolution element in the direction of scan. Means are also provided for converting the ultrasound reflected from the body into an electrical representation of the slice of the body. Typically, although not necessarily, conversion of the reflected ultrasound back into an electrical signal is achieved using the same transducer, and receiver electronics are employed to convert these signals into a form suitable for display, such as a television-type display.

The present invention is preferably practiced as an equipment which includes a console and a portable scanning module. The console typically houses electronics and a display, and the portable scanning module is suitable for being hand held and comprises a fluid-tight fluid-containing enclosure having a window that is placed in contact with the body being examined. The scanning module houses, among other things, the transducer, focusing means, an energizer/receiver coupled to the transducer, and means for effecting a mechanical scan of the beam through the scanning window. Typically, prior art systems employed a flexible window which hopefully conformed in shape to the body being examined to avoid liquid/air interfaces that might undesirably reflect ultrasound. In the present invention, a relatively narrow elongated scanning window is employed. This window configuration allows use of a relatively rigid window material since good contact with the body can be achieved over the window surface.

In one form of the invention, the transducer is pivotally mounted in the fluid-containing module and the means for scanning the ultrasonic beam is a motor for mechanically oscillating the transducer. The elongated generally elliptical configuration of the transducer renders its moment of inertia in the fluid sufficiently small that it can be mechanically oscillated without undue power being required, and with a substantial reduction in power as compared to that which would be required for a conventional transducer shape.

In another form of the invention the transducer is mounted at a stationary position in the fluid-containing module, and the means for scanning the ultrasonic beam is a scanning reflector spaced from the transducer. In this embodiment, the scanning reflector preferably has an elongated reflective surface which is elongated in the direction corresponding to the direction of elongation of the ultrasound beam incident thereon. Again, this shape of the reflector is advantageous in that it has a relatively low moment of inertia about its axis and is relatively easy to drive in the fluid.

In the preferred embodiment of the invention, the window through which scanning is effected is inclined at an angle with respect to the normal to the ultrasound incident thereon. This incline tends to cause any ultrasound that is undesirably internally reflected from the window to miss the transducer. In this embodiment, an absorbing medium, such as syntactic foam, is disposed on a wall in the module to absorb ultrasound internally reflected from the inclined window.

Further features and advantages of the invention will become more readily apparent from the following detailed description when taken in conjunction with the accompanying drawings.

DESCRIPTION OF THE PREFERRED EMBODIMENT

Figure 1:
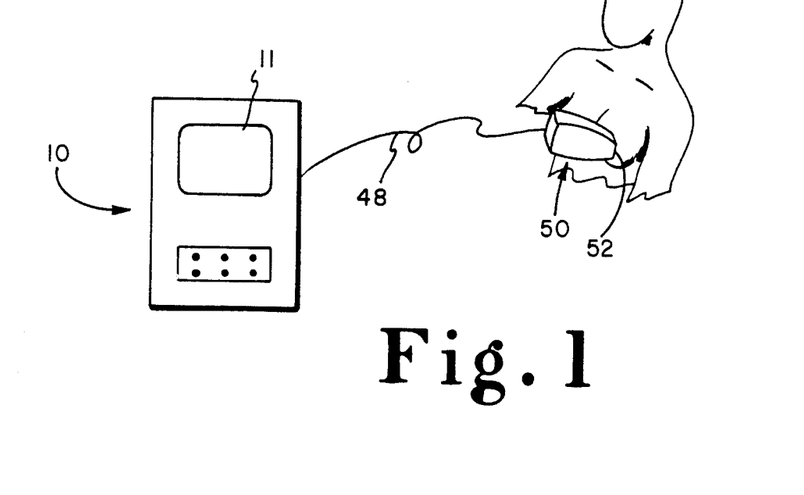
FIG. 1 illustrates the operation of a scanning apparatus which employs the improvements of the invention.
Figure 2:
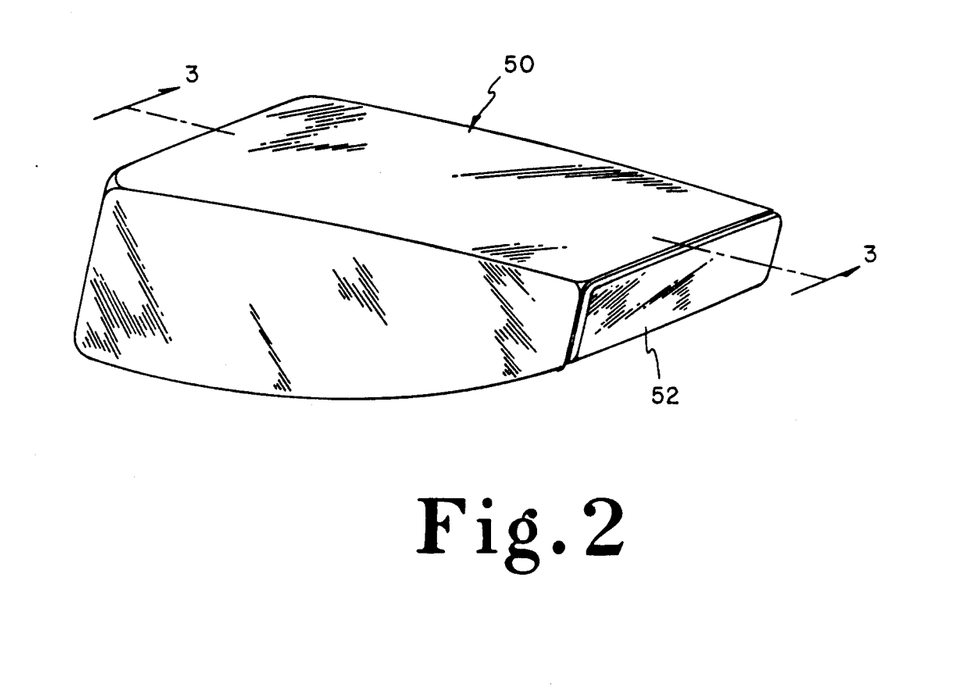
FIG. 2 is an elevational perspective view of an embodiment of the scanning module of the FIG. 1 apparatus.

Referring to FIG. 1, there is shown an illustration of a scanning apparatus which employs the improvements of the invention. A console 10 is provided with a display 11 which may typically be a cathode ray tube television-type display, and a suitable control panel. A video tape recorder or suitable photographic means may also be included in the console. The console will also typically house power supplies and portions of the timing and processing circuitry of the system, to be described. A portable scanning module or probe 50 is coupled to the console by cable 48. The scanning module 50, also shown in FIGS. 2 and 3, has a window 52 at one end thereof through which an investigating ultrasound beam is emitted and a reflected beam is received. During operation of the apparatus, the scanning module 50 is hand held to position the window 52 over a part of the body to be imaged. For example, in FIG. 1 the scanning module is positioned such that a cross section through a breast will be obtained. Imaging of other sections through the breast or other portions of the body is readily attained by moving the probe to the desired position and orientation, the relative orientation of the scanning window determining the angle of the cross section taken.

Figure 3:
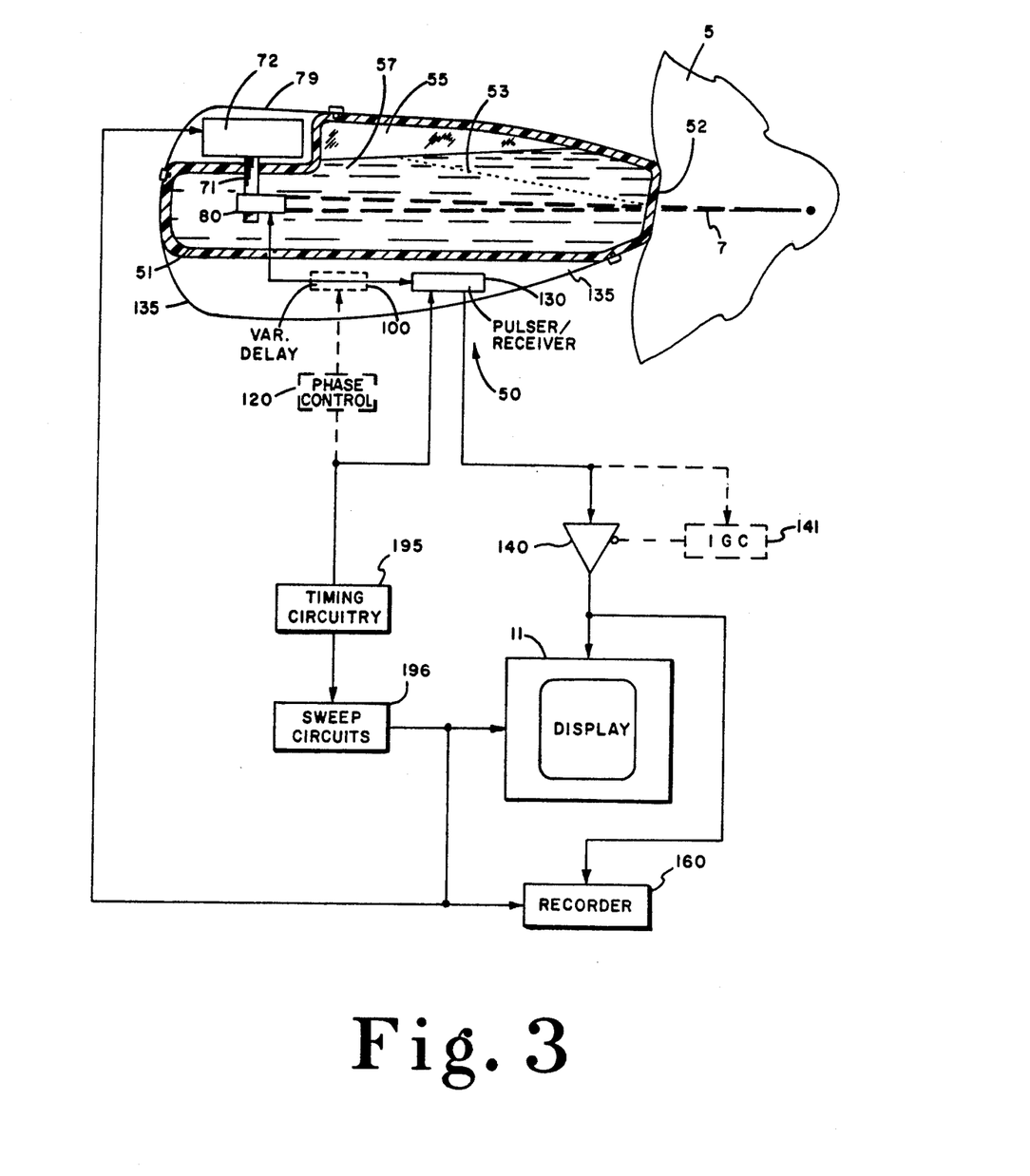
FIG. 3 shows a cross-sectional view of the scanning module of FIG. 2 as taken through a section defined by arrows 3—3, along with diagrams of portions of circuitry therein and in the accompanying console.

Referring to FIG. 3, there is shown a cross-sectional view of a portion of the scanning module or probe 50 along with diagrams of portions of the circuitry therein and in console 10 (FIG. 1) used in conjunction therewith. A fluid-tight enclosure 51, which may be formed of a sturdy plastic, has scanning window 52 at the front end thereof. The enclosure 51 is filled with a suitable fluid 57, for example water. In the present embodiment the scanning window 52 is rigid and relatively flat and may be formed of any suitable material, for example methyl methacrylate or nylon.

Figure 4:
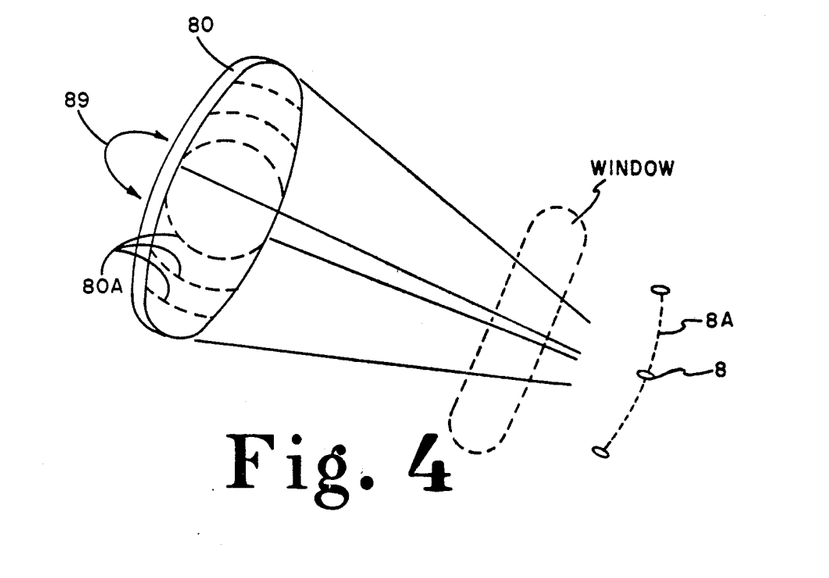
FIG. 4 illustrates the scan of the beam from the transducer of the scanning module of FIG. 2.
Figure 5:
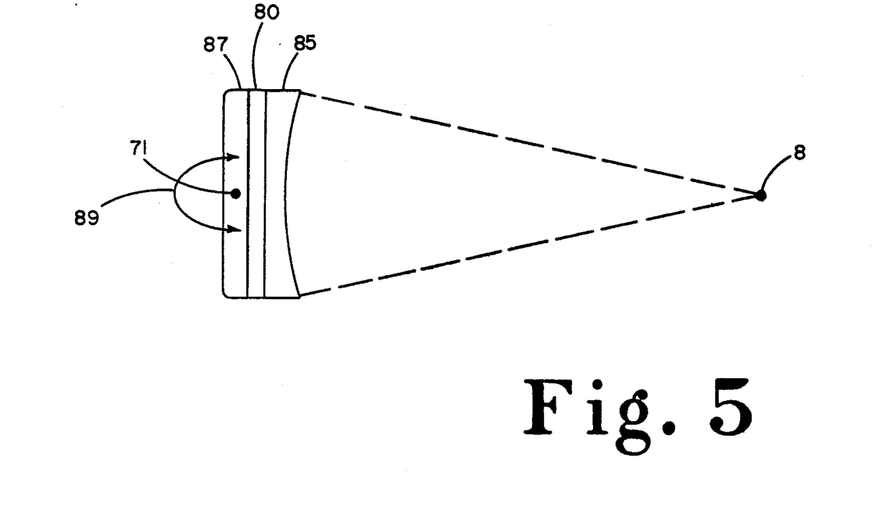
FIG. 5 illustrates the transducer, lens and backing layer of the scanning module of FIG. 2.

An ultrasonic transducer 80 is pivotally mounted on a shaft 71. The shaft 71 passes through a suitable seal in enclosure 51 where it is coupled to a motor 72, typically a small electric motor, which is mounted on the outside of fluid-tight enclosure 51 and is suitably driven to provide oscillatory motion of transducer 80. The motor 72 may be mounted in a shoulder formed on the enclosure 51, as shown in the FIGURE, and provided with a cover to avoid irregularity in the outer shape of scanning module 50. As seen in FIG. 4, the transducer 80 is elongated along the direction of scan, the transducer of this embodiment having a generally elliptical shape. Preferably, the transducer length-to-width aspect ratio is at least two to one. In the present embodiment, a focusing lens 85 is bonded to the front of the transducer 80 and has a curved concave surface which provides focusing. The lens has a thickness which is axially symmetrical, generally either spherical or an ellipsoid of revolution. The lens is preferably elliptical in circumference to conform to the shape of the transducer and may be formed, for example, of a plastic material with the material being selected in accordance with the principles set forth in the U.S. Pat. No. 3,958,559, assigned to the same assignee as the present application. As disclosed in that patent, by selecting the lens material in accordance with specified parameters, "apodization" is achieved; i.e., undesired s lobes, caused by factors such as finite transducer size, are minimized. It will be understood that alternative means of focusing can be employed, such as an electronic focusing using a segmented transducer, or providing curvature in the transducer surface. In such cases, the focusing should be axially symmetrical over the transducer area. In the present embodiment a backing layer 87 is bonded to the rear surface of transducer 80, and this backing layer is mounted on shaft 71 so that the backing layer, transducer, and lens can oscillate in the manner indicated by arrow 89 of FIG. 5. FIG. 4 illustrates the nature of the scan of beam 7, indicated by the motion of the scanning spot 8 along dashed line 8A. After focusing by lens 85 (FIG. 5), which is bonded to transducer 80 and preferably conforms circumferentially in shape thereto, the resultant spot 8 is elongated in a direction normal to the direction of scan, since the diffraction limit in the transducer elongation direction is smaller than the diffraction limit in the direction orthogonal thereto. The thickness of the investigated "slice" is therefore substantially larger (preferably at least twice as large) as a resolution element in the direction of scan.

A pulser/receiver circuit 130 alternately provides energizing pulses to and receives echo signals from the transducer 80. As used herein, the term pulser/receiver is intended to include any combined or separate circuits for producing the energizing signals for the transducer and receiving echo signals therefrom. If dynamic focusing is employed, the transducer 80 may be segmented, as illustrated by the lines 80A in FIG. 4, and the pulser/receiver circuitry 130 may be coupled to the segments of transducer 80 via variable delay circuitry 100, shown in dashed line. The pulser/receiver circuitry 130 and the variable delay circuitry 100 (if present) are typically, although not necessarily, located in the scanning module 50, for example within the region defined by a cover 135 which may be secured to the fluid-tight enclosure 51 by any suitable means. The receiver portion of circuit 130 is coupled through an amplifier 140 to display 11 and to recorder 160, which may be any suitable recording, memory, and/or photographic means, for example a video tape recorder. If desired, gain control circuitry including an interactive gain compensation ("IGC") capability, as represented by the block 141 (shown in dashed line), can be employed. Interactive gain compensation techniques are described in detail in the U.S. Pat. No. 4,043,181, assigned to the same assignee as the present application. This circuitry compensates the amplitude of later arriving signals for attenuation experienced during passage through body tissue and losses due to prior reflections. Accordingly, if an IGC capability is employed, the amplifier 140 may be used as a gain control amplifier under control of an IGC signal from circuit 141. Timing circuitry 195 generates timing signals which synchronize operation of the system, the timing signals being coupled to pulser/receiver 130 and also to sweep circuitry 196 which generates the signals that control the oscillatory action caused by motor 72 and the vertical and horizontal sync signals for the display 11 and recorder 160. If dynamic focusing is employed, as described in copending U.S. patent application Ser. No. 665,898, assigned to the same assignee as the present application, the timing signals may also be coupled to phase control circuitry 120 which produces signals that control the variation of the delays in variable delay circuit 100.

Operation of the system of FIG. 3 is as follows: Upon command from the timing circuits the pulser in circuitry 130 generates pulses which excite the transducer 80, the segments of transducer 80 being excited via variable delay circuitry 100, under control of phase control circuitry 120, when dynamic focusing is employed. (As is known in the art, the depth of focus can be varied electronically in a dynamically focused system by imparting predetermined delays or phase changes to different segments of the transducer 80. In such case, the ultrasound pulse is typically launched with the variable delay circuitry set so that the transmitted beam is focused at a point which is between the center of the field and the deepest point within the body which an image is being sought.) The beam 7 of ultrasound resulting from pulsing the transducer is transmitted through the window 52 and into the body 5. The timing circuitry now causes the pulser/receiver 130 to switch into a "receive" or "listen" mode. (If dynamic focusing is employed, a cycle of the phase control circuitry 120 is activated.) Now, as the ultrasound echoes are received from the body via window 52, the transducer serves to convert the received ultrasound energy into electrical signals. (Again, for a dynamic focusing implementation, the transducer segments serve to convert the received ultrasound energy into electrical signals which are combined in proper phase relationship for focusing on particular reflection origination points in the range of depths being investigated.) For a two-dimensional "B-scan" display, a sweep over the range of depth corresponds to a horizontal scanline of the display, so the timing signals from circuitry 196 synchronize the horizontal sync of the display such that the active portion of one scanline of the display corresponds to the time of arrival of echoes from a given range within the body 5, typically from the patient's skin up to a fixed preselected depth in the body. The second dimension of the desired cross-sectional image is attained by the slower mechanical scan of transducer 80, as illustrated in FIG. 4. The torque required to drive the transducer (along with backing and lens in this embodiment) is strongly dependent upon its size and mass, and an advantage of the present configuration, as compared to conventional transducer shapes, is the reduction in power needed to drive the transducer. This allows a configuration as set forth in FIG. 3 wherein the transducer is directly oscillated in the fluid.

In accordance with a feature of the invention the window 52 is inclined at an angle, for example an angle of the order of 10°, with respect to the normal to the ultrasound incident thereon. This incline tends to cause any ultrasound that is undesirably reflected from the window (which is preferably formed of a relatively rigid material, as described above) to miss the transducer. An absorbing medium 55, which may, for example, be syntactic foam, is disposed in the path of internally reflected ultrasound, represented in FIG. 3 by the dotted line 53. In the present embodiment the window is inclined toward the top of module 50 and the absorbing medium 55 is disposed on the top inner surface of enclosure 51.

Figure 6:
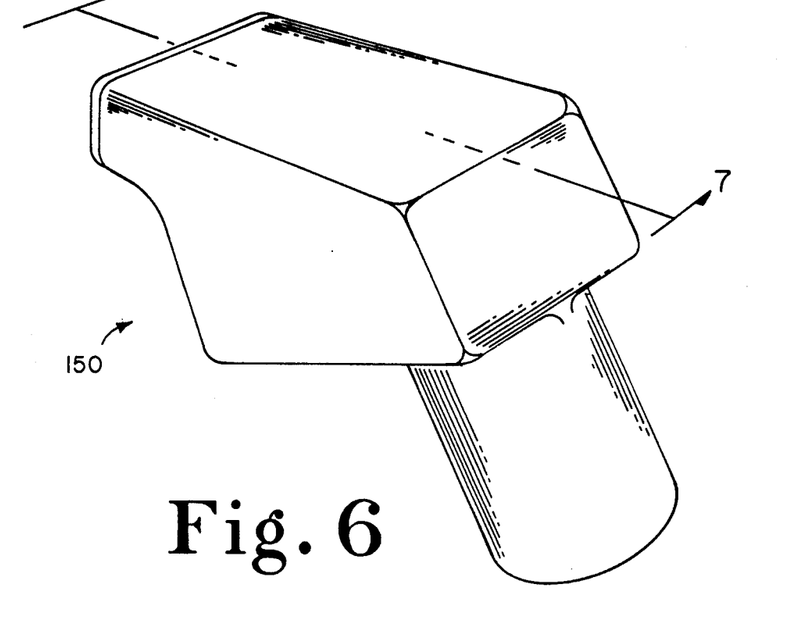
FIG. 6 is an elevational perspective view of the scanning module in accordance with another embodiment of the invention.
Figure 7:
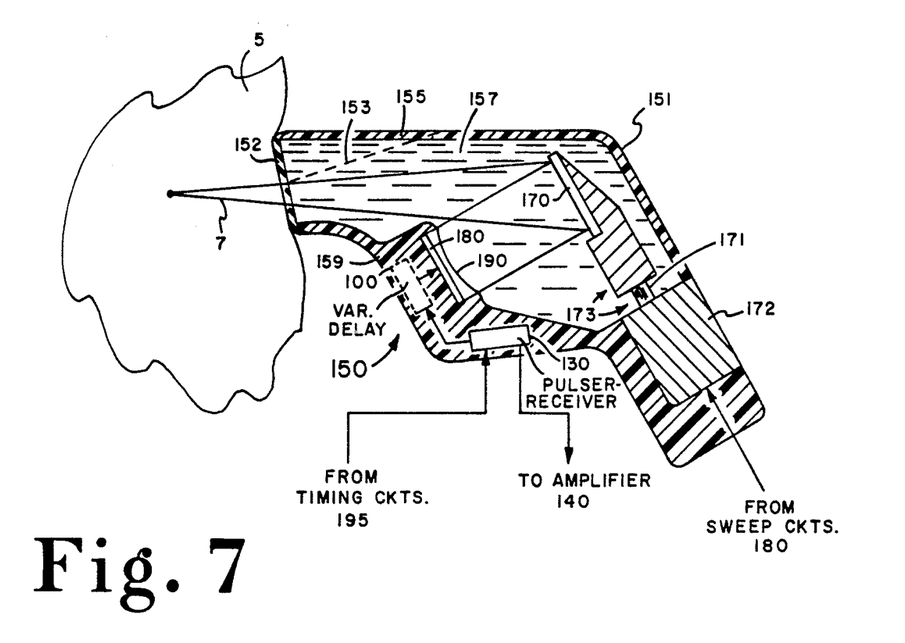
FIG. 7 is a cross-sectional view as taken through a section defined by arrows 7—7 of FIG. 6.

Referring to FIGS. 6 and 7, there is shown another embodiment of a scanning module 150 in accordance with the invention. The scanning module may also typically be used in conjunction with the console of FIG. 1 and with electronics similar to those illustrated in conjunction with FIG. 3. In this embodiment, a fluid-tight fluid-filled enclosure 151 again has a scanning window, labeled 152, at the front end thereof. The scanning window is elongated and inclined to provide the same advantages described above in conjunction with the embodiment of FIG. 3. A reflective scanner 170, which is flat in the present embodiment but which may be curved to provide focusing if desired, is positioned at the approximate rear of enclosure 151 and substantially faces the window 152. The scanner 170 is mounted on a shaft 171 which passes through a suitable seal and is connected to an electric motor 172 that is mounted in a recess in enclosure 51 and is driven to provide the desired oscillatory motion of scanner 170, as depicted by the curved two-headed arrow 173.

Figure 8:
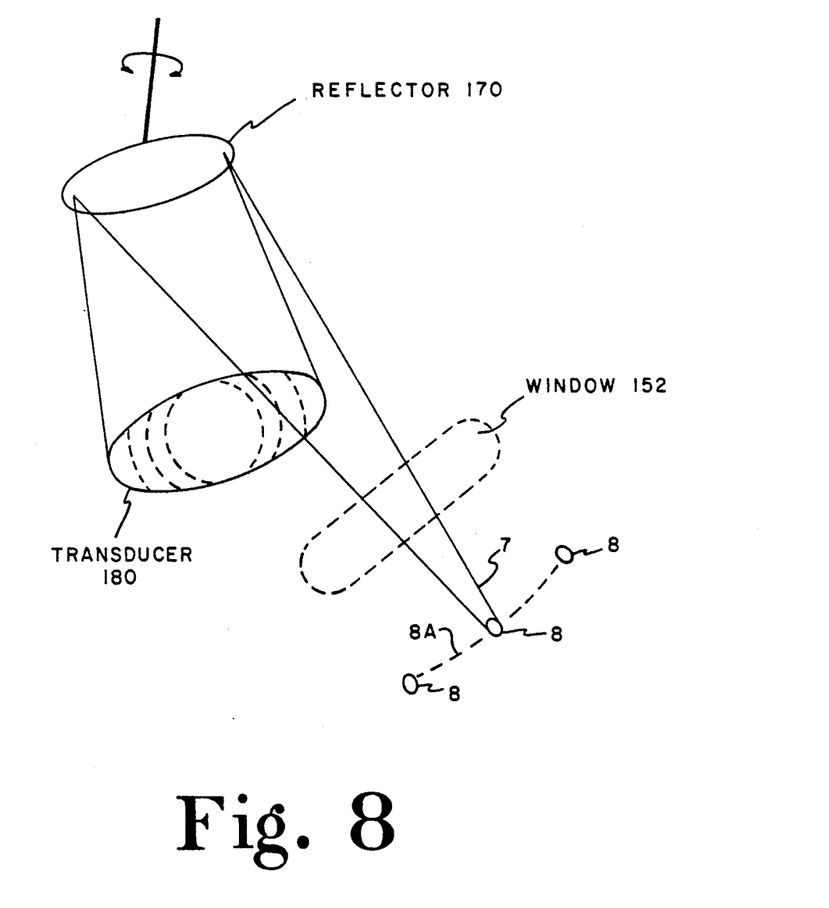
FIG. 8 illustrates the scan of the beam from the transducer and reflector of the scanning module of FIGS. 6 and 7.

An ultrasonic transducer 180 is mounted in a compartment 159 of enclosure 151 (the compartment also housing the electronics), the transducer being mounted relatively frontwardly of reflective scanner in the module 150 with the ultrasound-emitting face of the transducer generally facing rearwardly in the module 150 and being directed toward the reflective scanner 170. The transducer 180 has a generally elliptical elongated configuration of the type illustrated in FIG. 4, and has a focusing lens 190 bonded thereto. In accordance with principles set forth in my above-referenced copending U.S. patent application Ser. No. 890,378, the transducer 180 is positioned such that the ultrasound beam which it emits is reflected by the scanner 170 to double back past transducer 180 before passing through the window 152. As described in the referenced copending application, the ultrasound beam subtends an angle at the reflective scanner which is relatively acute, and this can be achieved by providing a reflective surface on scanner 170 that has a relatively small critical angle so that the beam impinging almost directly on the reflector surface will not pass through the reflector. A suitable surface material is sapphire. As described in the referenced copending application, the arrangement set forth makes particularly efficient use of the volume of fluid 157 in the module 150 since the beam 7 is effectively "doubling back" past the transducer as experiencing a relatively large travel distance through a relatively small volume of water. Various considerations, including minimizing artifacts which might otherwise be produced by reflection of ultrasound from the skin and then off the transducer, dictate a certain minimum distance from the transducer to the object being scanned. Using the configuration set forth, distance considerations are met while still employing a relatively small and compact scanning module. The window 152 is preferably inclined to obtain the advantages described in conjunction with the FIG. 3 embodiment, and an absorbing medium 155 is provided to absorb internally reflected ultrasound, represented by the dotted line 153. Operation of the embodiment of FIGS. 6 and 7 is similar to that of the FIG. 3 embodiment except that scanning is effected by the reflective scanner 170 instead of by movement of the transducer. FIG. 8 illustrates the nature of the scan of beam 7, indicated by the motion of the scanning spot 8 along dashed line 8A. The elongated reflector 170 has a generally elliptical shape, as does the transducer 180. As stated above, the disclosed reflector shape is advantageous in that it has a relatively low moment of inertia about its axis and is relatively easy to drive in the fluid.

The invention has been described with reference to particular embodiments, but variations within the spirit and scope of the invention will occur to those skilled in the art. For example, some of the circuitry of the console may be housed in the scanning module, if desired, or vice versa, the basic consideration being the desire to maintain portability of the module while still minimizing the noise-susceptibility of low-level signals passing through cables between the scanning module and the console.

I claim:

1. Apparatus for ultrasonically investigating a slice of a body to obtain an image thereof, comprising:
   means for generating an energizing signal;
   a transducer coupled to said energizing means for generating a beam of ultrasonic energy;
   a focusing lens for focusing said beam, said lens having a thickness defined by a surface of revolution around the axis of said beam;
   means for scanning said beam across said body along the plane of the slice of the body to be imaged;
   said transducer having a periphery which is elongated along the direction of the scan, whereby the spot resulting from the focused ultrasonic beam is elongated in a direction normal to the direction of scan; and
   means for converting ultrasound reflected from said body into an electrical representation of said slice of the body.

2. Apparatus as defined by claim 1 wherein said transducer has a length-to-width aspect ratio of at least two to one.

3. Apparatus as defined by claim 2 wherein said means for scanning said ultrasonic beam comprises a scanning reflector spaced from said transducer.

4. Apparatus as defined by claim 3 wherein said scanning reflector has an elongated reflecting surface which is elongated in the direction corresponding to the direction of elongation of the ultrasonic beam incident thereon.

5. Apparatus as defined by claim 4 wherein said transducer and reflector are disposed in a fluid-containing housing having a window adapted for placement next to said body, and wherein said reflector is disposed in the fluid in the ultrasound path between said transducer and said window.

6. Apparatus as defined by claim 5 wherein said window is inclined at an angle with respect to the normal to the ultrasound incident on said window.

7. Apparatus as defined by claim 6 wherein said window is elongated in the scan direction of the ultrasonic beam incident thereon.

8. Apparatus as defined by claim 6 further comprising an ultrasound absorbing medium disposed in said housing in the path of ultrasound internally reflected from said inclined window.

9. Apparatus as defined by claim 5 wherein said window is elongated in the scan direction of the ultrasonic beam incident thereon.

10. Apparatus as defined by claim 2 wherein said transducer is pivotally mounted, on an axis substantially perpendicular to its length, in a fluid-containing housing, said housing having a window opposing said transducer and adapted for placement next to said body, and wherein said means for scanning said ultrasonic beam comprises means for mechanically oscillating said transducer.

11. Apparatus as defined by claim 10 wherein said window is inclined at an angle with respect to the normal to the ultrasound incident on said window.

12. Apparatus as defined by claim 11 wherein said window is elongated in the scan direction of the ultrasonic beam incident thereon.

13. Apparatus as defined by claim 10 wherein said window is elongated in the scan direction of the ultrasonic beam incident thereon.

14. Apparatus as defined by claim 1 wherein the periphery of said transducer has a generally elliptical shape.

15. Apparatus as defined by claim 14 wherein said focusing means is a lens having a generally elliptical periphery which conforms in shape to the generally elliptical periphery of said transducer.

16. Apparatus as defined by claim 15 wherein said transducer includes annular sectors for use in dynamic focusing.

17. Apparatus as defined by claim 15 wherein said lens is bonded to said transducer.

18. Apparatus as defined by claim 14 wherein said transducer includes annular sectors for use in dynamic focusing.

19. Apparatus as defined by claim 1 wherein said means for scanning said ultrasonic beam comprises a scanning reflector spaced from said transducer.

20. Apparatus as defined by claim 19 wherein said scanning reflector has an elongated reflecting surface which is elongated in the direction corresponding to the direction of elongation of the ultrasonic beam incident thereon.

21. Apparatus as defined by claim 20 wherein said transducer and reflector are disposed in a fluid-containing housing having a window adapted for placement next to said body, and wherein said reflector is disposed in the fluid in the ultrasound path between said transducer and said window.

22. Apparatus as defined by claim 21 wherein said window is inclined at an angle with respect to the normal to the ultrasound incident on said window.

23. Apparatus as defined by claim 2 wherein said window is elongated in the scan direction of the ultrasonic beam incident thereon.

24. Apparatus as defined by claim 22 further comprising an ultrasound absorbing medium disposed in said housing in the path of ultrasound internally reflected from said inclined window.

25. Apparatus as defined by claim 21 wherein said window is elongated in the scan direction of the ultrasonic beam incident thereon.

26. Apparatus as defined by claim 25 further comprising an ultrasound absorbing medium disposed in said housing in the path of ultrasound internally reflected from said inclined window.

27. Apparatus as defined by claim 1 wherein said transducer is pivotally mounted, on an axis substantially perpendicular to its length, in a fluid-containing housing, said housing having a window opposing said transducer and adapted for placement next to said body, and wherein said means for scanning said ultrasonic beam comprises means for mechanically oscillating said transducer.

28. Apparatus as defined by claim 27 wherein said window is inclined at an angle with respect to the normal to the ultrasound incident on said window.

29. Apparatus as defined by claim 28 wherein said window is elongated in the scan direction of the ultrasonic beam incident thereon.

30. Apparatus as defined by claim 29 further comprising an ultrasound absorbing medium disposed in said housing in the path of ultrasound internally reflected from said inclined window.

31. Apparatus as defined by claim 28 further comprising an ultrasound absorbing medium disposed in said housing in the path of ultrasound internally reflected from said inclined window.

32. Apparatus as defined by claim 27 wherein said window is elongated in the scan direction of the ultrasonic beam incident thereon.

33. Apparatus as defined by claim 1 wherein said focusing lens has an elongated periphery which conforms in shape to the periphery of said transducer.

34. Apparatus as defined by claim 1 wherein said transducer includes annular sectors for use in dynamic focusing.

35. In an apparatus for ultrasonically imaging sections of a body by transmitting ultrasonic energy into the body and determining the characteristics of the ultrasonic energy reflected therefrom, said apparatus including timing means for generating timing signals; energizing/receiving means alternately operative in response to timing signals; and display/record means synchronized with said timing signals for displaying and/or recording image-representative signals from the energizing/receiving means; an improved portable scanning module, comprising:

a fluid-tight enclosure having a scanning window;
fluid means contained in said enclosure;

a transducer for converting energy from said energizing/receiving means to periodic ultrasonic energy and for converting reflected ultrasonic energy to electrical signals, said transducer having an elongated generally elliptical periphery; and means for scanning said beam across said body along the plane of the slice of the body to be imaged.

36. Apparatus as defined by claim 35 wherein said transducer and window each have a length-to-width aspect ratio of at least two to one.

37. Apparatus as defined by claim 36 wherein said means for scanning said beam comprises a scanning reflector disposed in said fluid means, said scanning reflector having an elongated reflecting surface which is elongated in the direction of elongation of the ultrasound beam incident thereon.

38. Apparatus as defined by claim 35 wherein said window is inclined at an angle with respect to the normal to the ultrasound incident on said window.

39. Apparatus as defined by claim 38 wherein said means for scanning said beam comprises a scanning reflector disposed in said fluid means, said scanning reflector having an elongated reflecting surface which is elongated in the direction of elongation of the ultrasound beam incident thereon.

40. Apparatus as defined by claim 35 wherein said means for scanning said beam comprises a scanning reflector disposed in said fluid means, said scanning reflector having an elongated reflecting surface which is elongated in the direction of elongation of the ultrasound beam incident thereon.

41. Apparatus as defined by claim 40 wherein said transducer and window each have a length-to-width aspect ratio of at least two to one.

42. Apparatus as defined by claim 41 further comprising an ultrasound absorbing medium disposed in said housing in the path of ultrasound internally reflected from said inclined window.

43. Apparatus as defined by claim 35 wherein said transducer includes annular sectors for use in dynamic focusing.

44. Apparatus for ultrasonically investigating a slice of a body to obtain an image thereof, comprising:
means for generating an energizing signal;
a transducer coupled to said energizing means for generating a beam of ultrasonic energy;
means for scanning said beam across said body along the plane of the slice of the body to be imaged;
said transducer having a periphery of generally elliptical shape which is elongated along the direction of the scan, whereby the spot resulting from the focused ultrasonic beam is elongated in a direction normal to the direction of scan; and
means for converting ultrasound reflected from said body into an electrical representation of said slice of the body.

45. Apparatus as defined by claim 44 wherein said transducer has a length-to-width aspect ratio of at least two to one.

46. Apparatus as defined by claim 44 wherein said means for scanning said ultrasonic beam comprises a scanning reflector spaced from said transducer.

47. Apparatus as defined by claim 46 wherein said scanning reflector has an elongated reflecting surface which is elongated in the direction corresponding to the direction of elongation of the ultrasonic beam incident thereon.

48. Apparatus as defined by claim 47 wherein said transducer and reflector are disposed in a fluid-containing housing having a window adapted for placement next to said body, and wherein said reflector is disposed in the fluid in the ultrasound path between said transducer and said window.

49. Apparatus as defined by claim 48 wherein said window is inclined at an angle with respect to the normal to the ultrasound incident on said window.

50. Apparatus as defined by claim 49 wherein said window is elongated in the scan direction of the ultrasonic beam incident thereon.

51. Apparatus as defined by claim 49 further comprising an ultrasound absorbing medium disposed in said housing in the path of ultrasound internally reflected from said inclined window.

52. Apparatus as defined by claim 48 wherein said window is elongated in the scan direction of the ultrasonic beam incident thereon.

53. Apparatus as defined by claim 52 wherein said window is formed of a rigid material.

54. In an apparatus the ultrasonically imaging sections of a body by transmitting ultrasonic energy into the body and determining characteristics of the ultrasonic energy reflected therefrom, said apparatus including timing means for generating timing signals; energizing/receiving means alternately operative in response to timing signals; and display/record means synchronized with said timing signals for displaying and/or recording image-representative signals from the energizing/receiving means; an improved portable scanning module, comprising:
a fluid-tight enclosure having a scanning window;
fluid means contained in said enclosure;
transducer means for converting energy from said energizing/receiving means to a periodic ultrasonic energy beam and for converting reflected ultrasonic energy to electrical signals, said transducer means having an elongated configuration in the plane perpendicular to the beam emitted therefrom, said configuration having a width at its longitudinal center that is greater than the width at its longitudinal ends; and
means for scanning said beam across said body along the plane of the slice of the body to be imaged.

55. Apparatus as defined by claim 54 wherein said transducer means and window each have a length-to-width aspect ratio of at least two to one.

56. Apparatus as defined by claim 55 wherein said means for scanning said beam comprises a scanning reflector disposed in said fluid means, said scanning reflector having an elongated reflecting surface which is elongated in the direction of elongation of the ultrasound beam incident thereon, said scanning reflector having a width at its longitudinal center which is greater than the width at its longitudinal ends.

57. Apparatus as defined by claim 56 wherein said scanning reflector is pivotally mounted in said fluid means on an axis substantially perpendicular to its length, and wherein said means for scanning said beam includes means for oscillating said reflector.

58. Apparatus as defined by claim 57 wherein said reflective scanner has a generally elliptical periphery.

59. Apparatus as defined by claim 55 wherein said transducer means is pivotally mounted in said fluid means on an axis substantially perpendicular to its length, and wherein said means for scanning said beam comprises means for oscillating said transducer.

60. Apparatus as defined by claim 55 wherein said transducer means has a generally elliptical periphery.

61. Apparatus as defined by claim 54 wherein said means for scanning said beam comprises a scanning reflector disposed in said fluid means, said scanning reflector having an elongated reflecting surface which is elongated in the direction of elongation of the ultrasound beam incident thereon, said scanning reflector having a width at its longitudinal center which is greater than the width at its longitudinal ends.

62. Apparatus as defined by claim 61 wherein said scanning reflector is pivotally mounted in said fluid means on an axis substantially perpendicular to its length, and wherein said means for scanning said beam includes means for oscillating said reflector.

63. Apparatus as defined by claim 62 wherein said reflective scanner has a generally elliptical periphery.

64. Apparatus as defined by claim 61 wherein said reflective scanner has a generally elliptical periphery.

65. Apparatus as defined by claim 54 wherein said transducer means is pivotally mounted in said fluid means on an axis substantially perpendicular to its length, and wherein said means for scanning said beam comprises means for oscillating said transducer.

66. Apparatus as defined by claim 65 wherein said transducer means has a generally elliptical periphery.

67. Apparatus as defined by claim 54 wherein said transducer means has a generally elliptical periphery.

68. Apparatus for ultrasonically investigating a slice of a body to obtain an image thereof, comprising:
means for generating an energizing signal;
a transducer coupled to said energizing means for generating a beam of ultrasonic energy;
axially symmetrical focusing means for focusing said beam;
means for scanning said beam across said body along the plane of the slice of the body to be imaged;
said transducer having a generally elliptical periphery which is elongated along the direction of the scan, whereby the spot resulting from the focused ultrasonic beam is elongated in a direction normal to the direction of scan; and
means for converting ultrasound reflected from said body into an electrical representation of said slice of the body.

69. Apparatus as defined by claim 68 wherein said transducer has a length-to-width aspect ratio of at least two to one.

70. Apparatus as defined by claim 69 wherein said means for scanning said ultrasonic beam comprises a scanning reflector spaced from said transducer.

71. Apparatus as defined by claim 70 wherein said scanning reflector has an elongated reflecting surface which is elongated in the direction corresponding to the direction of elongation of the ultrasonic beam incident thereon.

72. Apparatus as defined by claim 71 wherein said transducer and reflector are disposed in a fluid-containing housing having a window adapted for placement next to said body, and wherein said reflector is disposed in the fluid in the ultrasound path between said transducer and said window.

73. Apparatus as defined by claim 72 wherein said window is inclined at an angle with respect to the normal to the ultrasound incident on said window.

74. Apparatus as defined by claim 72 wherein said window is elongated in the scan direction of the ultrasonic beam incident thereon.

75. Apparatus as defined by claim 69 wherein said transducer is pivotally mounted, on an axis substantially perpendicular to its length, in a fluid-containing housing, said housing having a window opposing said transducer and adapted for placement next to said body, and wherein said means for scanning said ultrasonic beam comprises means for mechanically oscillating said transducer.

76. Apparatus as defined by claim 75 wherein said window is elongated in the scan direction of the ultrasonic beam incident thereon.

77. Apparatus as defined by claim 69 wherein said focusing means is a lens having an elliptical periphery which conforms in shape to the elliptical periphery of said transducer.

78. Apparatus as defined by claim 77 wherein said transducer includes annular sectors for use in dynamic focusing.

79. Apparatus as defined by claim 69 wherein said focusing means is a lens having a thickness defined by a surface of revolution around said beam.

80. Apparatus as defined by claim 69 wherein said transducer includes annular sectors for use in dynamic focusing.

81. Apparatus as defined by claim 68 wherein said means for scanning said ultrasonic beam comprises a scanning reflector spaced from said transducer.

82. Apparatus as defined by claim 81 wherein said scanning reflector has an elongated reflecting surface which is elongated in the direction corresponding to the direction of elongation of the ultrasonic beam incident thereon.

83. Apparatus as defined by claim 82 wherein said transducer and reflector are disposed in a fluid-containing housing having a window adapted for placement next to said body, and wherein said reflector is disposed in the fluid in the ultrasound path between said transducer and said window.

84. Apparatus as defined by claim 83 wherein said window is inclined at an angle with respect to the normal to the ultrasound incident on said window.

85. Apparatus as defined by claim 83 wherein said window is elongated in the scan direction of the ultrasonic beam incident thereon.

86. Apparatus as defined by claim 68 wherein said tranducer is pivotally mounted, on an axis substantially perpendicular to its length, in a fluid-containing housing, said housing having a window opposing said transducer and adapted for placement next to said body, and wherein said means for scanning said ultrasonic beam comprises means for mechanically oscillating said transducer.

87. Apparatus as defined by claim 86 wherein said window is elongated in the scan direction of the ultrasonic beam incident thereon.

88. Apparatus as defined by claim 68 wherein said focusing means is a lens having an elliptical periphery which conforms in shape to the elliptical periphery of said transducer.

89. Apparatus as defined by claim 68 wherein said focusing means is a lens having a thickness defined by a surface of revolution around said beam.

90. Apparatus as defined by claim 68 wherein said transducer includes annular sectors for use in dynamic focusing.

91. In an apparatus the ultrasonically imaging sections of a body by transmitting ultrasonic energy into the body and determining characteristics of the ultrasonic energy reflected therefrom, said apparatus including timing means for generating timing signals; energizing/receiving means alternately operative in response to timing signals; and display/record means synchronized with said timing signals for displaying and/or recording image-representative signals from the energizing/receiving means; an improved portable scanning module, comprising:

a fluid-tight enclosure having a scanning window;

fluid means contained in said enclosure;

transducer means, having a generally elliptical periphery, for converting energy from said energizing/receiving means to periodic ultrasonic energy and for converting reflected ultrasonic energy to electrical signals; and means for scanning said beam across said body along the plane of the slice of the body to be imaged.

92. Apparatus ad defined by claim 91 wherein said transducer and window each have a length-to-width aspect ratio of at least two to one.

93. Apparatus as defined by claim 92 wherein said means for scanning said beam comprises a scanning reflector disposed in said fluid means, said scanning reflector having an elongated reflecting surface which is elongated in the direction of elongation of the ultrasound beam incident thereon, said scanning reflector having a width at its longitudinal center which is greater than the width at its longitudinal ends.

94. Apparatus as defined by claim 93 wherein said scanning reflector is pivotally mounted in said fluid means on an axis substantially perpendicular to its length, and wherein said means for scanning said beam includes means for oscillating said reflector.

95. Apparatus as defined by claim 94 wherein said reflective scanner has a generally elliptical periphery.

96. Apparatus as defined by claim 92 wherein said transducer means is pivotally mounted in said fluid means on an axis substantially perpendicular to its length, and wherein said means for scanning said beam comprises means for oscillating said transducer.

97. Apparatus as defined by claim 91 wherein said means for scanning said beam comprises a scanning reflector disposed in said fluid means, said scanning reflector having an elongated reflecting surface which is elongated in the direction of elongation of the ultrasound beam incident thereon, said scanning reflector having a width at its longitudinal center which is greater than the width at its longitudinal ends.

98. Apparatus as defined by claim 97 wherein said scanning reflector is pivotally mounted in said fluid means on an axis substantially perpendicular to its length, and wherein said means for scanning said beam includes means for oscillating said reflector.

99. Apparatus as defined by claim 98 wherein said reflective scanner has a generally elliptical periphery.

100. Apparatus as defined by claim 97 wherein said reflective scanner has a generally elliptical periphery.

101. Apparatus as defined by claim 91 wherein said transducer means is pivotally mounted in said fluid means on an axis substantially perpendicular to its length, and wherein said means for scanning said beam comprises means for oscillating said transducer.

* * * * *